United States Patent [19]

Steer

[11] Patent Number: 5,352,316

[45] Date of Patent: Oct. 4, 1994

[54] MEMBRANE, E.G. FOR USE IN AN ILEOSTOMY BAG

[75] Inventor: Graham E. Steer, London, England

[73] Assignee: E. R. Squibb & Sons, Inc., Princeton, N.J.

[21] Appl. No.: 747,086

[22] Filed: Aug. 19, 1991

[30] Foreign Application Priority Data

Aug. 22, 1990 [GB] United Kingdom ............... 9018411

[51] Int. Cl.⁵ .................... B32B 31/00; A61F 5/44
[52] U.S. Cl. .................... 156/252; 156/272.2; 156/278; 604/333
[58] Field of Search ............ 427/2, 290, 296; 156/252, 278, 272.2; 604/333

[56] References Cited

U.S. PATENT DOCUMENTS 4,120,715 10/1978 Ockwell et al. .
5,019,422 5/1991 Rose et al. .
5,074,851 12/1991 Plass et al. .

Primary Examiner—Chester T. Barry
Attorney, Agent, or Firm—Stuart E. Krieger

[57] ABSTRACT

A method of making a gas-permeable liquid-impermeable membrane includes the steps of perforating a film of linear low density polyethylene (or other suitable polyolefin) in such a way as to yield an array of holes each having an average diameter of approximately 350, microns and then solution coating the needled film with a porous polyurethane material having pores of a pore size of 1 to 10 microns.

Such a film is advantageously embodied in an ileostomy bag, and is fixed to a bag wall thereof in a location to prevent faecal material contacting the bag filter, by a heat or RF welding operation by which the polyolefin is welded to the bag wall which carries the filter. In use, the polyurethane is exposed to the bag contents, and permits gases to pass but prevents any liquid reaching the filter.

4 Claims, 1 Drawing Sheet

MEMBRANE, E.G. FOR USE IN AN ILEOSTOMY BAG

BACKGROUND OF THE INVENTION

This invention relates to a membrane, and particularly although not exclusively to a membrane which may be used in an ileostomy bag to prevent faecal material contacting a gas vent and filter in the bag wall, while allowing passage of flatus gases so that these, after being deodorised by passage through the filter, can escape to atmosphere.

A membrane useful for this purpose should desirably have holes of diameter (or maximum transverse dimension in the case of a non-circular hole) in the range 1 to $10\mu$, (microns). However, it is extremely difficult to make such small holes in currently available membrane films, and the thicker the film, the more difficult it is to make such small holes. However, the overall strength of the film is reduced to an undesirable level if its thickness is sufficiently small to enable holes of, say, less than $20\mu$ diameter to be made by conventional methods such as needling.

SUMMARY OF THE INVENTION

According to the invention, a method of making a gas-permeable liquid-impermeable membrane includes the steps of perforating a film of linear low density polyethylene (or other suitable polyolefin) in such a way as to yield an array of holes each having an average diameter of approximately $350\mu$, and then solution coating the needled film with a porous polyurethane material having pores of a pore size of 1 to $10\mu$.

Also according to the invention, such a film is embodied in an ileostomy bags and is fixed to a bag wall thereof in a location to prevent faecal material contacting the bag filter, by a heat or RF welding operation by which the polyolefin is welded to the bag wall which carries the filter. In use, the polyurethane is exposed to the bag contents, and permits gases to pass but prevents any liquid reaching the filter.

An important advantage of this invention is that such a film prevents the bag contents from contacting the filter and in manufacture the film can be heat welded to the bag walls using the same machinery that is used to join together the walls of the ileostomy bag by a peripheral weld. Hence the resulting bag is more efficient for its intended purpose and yet can be economically made.

In a preferred embodiment of the invention, the bag walls are made of a multi-laminate film having at least the layers e.v.a/gas barrier film/e.v.a. The intermediate layer serves two main purposes, firstly it acts as a gas barrier and secondly it increases the strength of the bag wall.

The perforation of the film of linear low density polyethylene may alternatively be done to yield holes whose minimum transverse dimension is in the range 300 to $400\mu$.

The polyethylene film may for example be $50\mu$ thick and have about 400 holes per square inch (2.4 million holes per sq. metre).

DESCRIPTION OF THE PREFERRED EMBODIMENT

Figure 1:
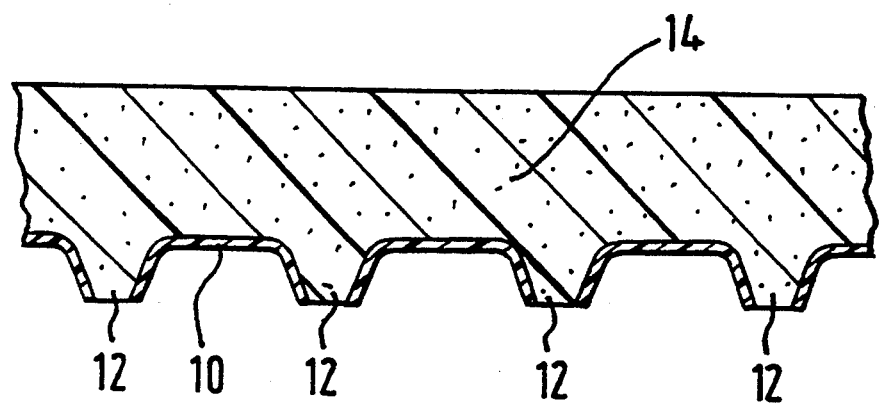
FIG. 1 is a diagrammatic cross sectional view of a membrane in accordance with the present invention.

FIG. 1 shows a film 10 of low density linear polyethylene provided with holes 12 by a vacuum perforation operation. The holes 12 are preferably approximately circular but could be of other shapes. Their diameter (or minimum transverse dimension) may be in the range 200 to $400\mu$ as stated.

Onto this film there is solution coated a porous polyurethane backing 14 which has connecting pores. The pore size is desirably 1 to $10\mu$ and preferably about 3 to $8\mu$. The resulting composite film may readily be rolled and die cut and, as stated, can be handled by conventional high speed ostomy bag making machinery.

The composite film is created by solution coating the vacuum perforated polyolefin with the polyurethane, the coating being such as to create microporous interlinked pores as described above. The two layers are held together using a suitable tie layer to create the finished structure. After drying to remove solvent, the finished construction can be reel wound ready for machine handling. It may be required for the polyurethane side of the finished structure to be treated with fluorocarbon to further enhance its fluid repellency. For such treatment one could use a commercially-available water-repellent coating.

The coated dried polyurethane coating preferably has a thickness in the range 10 to 15 microns.

What is claimed is:

1. A method for making a membrane to be used in a ileostomy pouch comprising:
   providing a linear low density polyolefin film capable of being heat welded or RF welded to the bag walls of an ileostomy pouch; said film being perforated with an array of holes each with an average diameter of 300–400 microns;
   coating said film with porous polyurethane having connecting pores ranging from 1–10 microns so as to make the coated film gas permeable and liquid impermeable;
   providing an ileostomy pouch having an opening for receiving waste material and a filter in said ileostomy pouch for deodorizing the waste material; and
   welding with heat or RF the coated film to the ileostomy pouch so as to cover the filter and permit gaseous waste material to pass through the filter while preventing liquid waste material from blocking the filter.

2. A method as claimed in claim 1, wherein the step of welding includes welding said polyolefin to the inside of said ileostomy pouch, and said polyolefin is polyethylene.

3. A product made pursuant to the method claimed in claim 1.

4. A product made pursuant to the method claimed in claim 2.

* * * * *